US008470348B2

(12) United States Patent
Blaeser et al.

(10) Patent No.: US 8,470,348 B2
(45) Date of Patent: Jun. 25, 2013

(54) SKIN CLEANSING AGENT, PARTICULARLY FOR REMOVING PRINTING INKS AND/OR SOILING CAUSED BY INK

(75) Inventors: Edeltraud Blaeser, Krefeld (DE); Marcel Veeger, Goch (DE); Annette Zur Muehlen, Krefeld (DE); Brigitte Thoerner, Dusseldorf (DE)

(73) Assignee: Evonik Degussa GmbH, Essen (DE)

( * ) Notice: Subject to any disclaimer, the term of this patent is extended or adjusted under 35 U.S.C. 154(b) by 350 days.

(21) Appl. No.: 10/572,574

(22) PCT Filed: Apr. 29, 2005

(86) PCT No.: PCT/EP2005/004633
§ 371 (c)(1), (2), (4) Date: Mar. 17, 2006

(87) PCT Pub. No.: WO2005/117826
PCT Pub. Date: Dec. 15, 2005

(65) Prior Publication Data
US 2007/0041927 A1    Feb. 22, 2007

(30) Foreign Application Priority Data
May 28, 2004   (DE) .......................... 10 2004 026 684

(51) Int. Cl.
*A61K 8/02* (2006.01)
(52) U.S. Cl.
USPC .......................................................... 424/401
(58) Field of Classification Search
USPC .......................................................... 424/401
See application file for complete search history.

(56) References Cited

U.S. PATENT DOCUMENTS

| | | | |
|---|---|---|---|
| 5,104,567 A | 4/1992 | Staehr | |
| 6,376,438 B1 | 4/2002 | Rosenberger et al. | |
| 6,471,983 B1 | 10/2002 | Veeger et al. | |
| 6,489,275 B1 | 12/2002 | Veeger et al. | |
| 7,163,916 B2 | 1/2007 | Allef et al. | |
| 7,241,452 B2 | 7/2007 | Veeger et al. | |
| 7,297,675 B2 | 11/2007 | Allef et al. | |
| 2003/0147825 A1* | 8/2003 | Chiarelli et al. ........... 424/70.11 | |
| 2004/0022862 A1* | 2/2004 | Kipp et al. .................... 424/490 | |
| 2004/0170592 A1 | 9/2004 | Veeger et al. | |
| 2005/0031580 A1 | 2/2005 | Allef et al. | |
| 2006/0165627 A1 | 7/2006 | Allef et al. | |
| 2006/0182690 A1 | 8/2006 | Veeger et al. | |
| 2006/0198859 A1 | 9/2006 | Allef et al. | |
| 2006/0204468 A1 | 9/2006 | Allef et al. | |
| 2007/0092470 A1 | 4/2007 | Allef et al. | |
| 2008/0145320 A1 | 6/2008 | Wenk et al. | |
| 2008/0305056 A1 | 12/2008 | Jenni et al. | |
| 2009/0054521 A1 | 2/2009 | Herrwerth et al. | |
| 2010/0069505 A1 | 3/2010 | Veeger et al. | |

FOREIGN PATENT DOCUMENTS

| | | |
|---|---|---|
| DE | 199 18 188 | 10/2000 |
| WO | 99 06021 | 2/1999 |
| WO | 99 19432 | 4/1999 |
| WO | 01 30315 | 5/2001 |
| WO | 03 026609 | 4/2003 |
| WO | 03 037270 | 5/2003 |

OTHER PUBLICATIONS

U.S. Appl. No. 12/595,531, filed Oct. 12, 2009, Allef, et al.
U.S. Appl. No. 12/446,569, filed Apr. 21, 2009, Veeger, et al.
U.S. Appl. No. 13/501,251, filed Apr. 11, 2012, Allef, et al.
U.S. Appl. No. 13/379,489, filed Dec. 20, 2011, Thoerner, et al.
U.S. Appl. No. 13/380,064, filed Dec. 22, 2011, Allef, et al.

* cited by examiner

*Primary Examiner* — Paul Zarek
(74) *Attorney, Agent, or Firm* — Oblon, Spivak, McClelland, Maier & Neustadt, L.L.P.

(57) ABSTRACT

The invention relates to a skin cleansing agent, particularly for the removal of printing colors and/or inks, comprising the components
a) 1 to 70 wt.-% of at least one ethoxylated amine and/or ethoxylated diamine,
b) 30 to 70 wt.-% of at least one polyethylene glycol of general formula $H-O-(CH_2CH_2-O)_n H$, wherein n is an integer of from 1 to 150,
c) 1 to 30 wt.-% of at least one fatty alcohol polyglycol ether,
d) 0.1 to 5 wt.-% of at least one complexing agent,
e) 0 to 30 wt.-% of at least one reducing or oxidizing agent,
f) 0 to 25 wt.-% of one or more abrasives,
g) 0 to 10 wt.-% of at least one polyhydric alcohol,
h) 0 to 3 wt.-% water,
i) optionally one or more viscosity-building agents,
j) optionally further cosmetic adjuvants, additives and/or active substances,
the sum of components a) through j) making 100 wt.-%, relative to the composition of the cleansing agent.

22 Claims, No Drawings

SKIN CLEANSING AGENT, PARTICULARLY FOR REMOVING PRINTING INKS AND/OR SOILING CAUSED BY INK

This application is a 371 of PCT/EP05/04633 filed Apr. 29, 2005.

The invention relates to a skin cleansing agent, particularly for cleaning extreme soiling of skin and hands caused e.g. by reducible or oxidizable printing colors and/or inks, especially printer inks.

Skin and hand cleansing agents find extensive use in the industry, especially in those cases where tenacious soiling occurs, which is caused by lacquers, fats, oils, lubricants, metal dusts, graphite, soot, but also by printing colors and/or inks.

For example, such cleansing agents are known as so-called coarse hand cleaners (see H. Tronnier, J. Kresken, K. Jablonski, B. Komp, "Haut und Beruf", Grosse Verlag, Berlin, pp. 75-108 [1989]). In general, these are formulations including an abrasive, surfactant/surfactant mixtures, thickening agents, and optionally auxiliary agents to control consistency, appearance, odor, and stability, such as pigments, odorous substances, stabilizers, and preservatives. In case of particularly tenacious soiling, there are products where the use of the above-mentioned ingredients is insufficient. Such formulations are added with organic solvents such as aliphatic hydrocarbons, terpenes, carboxylic esters of the dimethyl adipate, dimethyl glutarate, dimethyl succinate (DBE), and di-n-butyl adipate or diisopropyl adipate types, such as described in DE 43 35 933 A1.

Furthermore, reference is made to the so-called waterless cleaners available on the market, the good cleansing effect of which being predominantly based on the above-mentioned organic solvents, particularly gasolines, kerosenes, and short-chain paraffin oils. Thus, commercially available waterless cleaners have the following composition:
Petroleum distillates: 35.0 to 45.0 wt.-%
Water: 30.0 to 35.0 wt.-%
Mineral oils: 10.0 to 20.0 wt.-%
Sodium oleate: 10.0 to 20.0 wt.-%
Trideceth-9: 1.0 to 5.0 wt.-%
Propylene glycol: 1.0 to 5.0 wt.-%
Petrolatum: 1.0 to 5.0 wt.-%
Lanolin: 1.0 to 5.0 wt.-%
Zinc pyrithione: 0.1 to 1.0 wt.-%

Further examples of such solvent-containing "waterless cleaners" can be found in Ernest W. Flick, "Cosmetic and Toiletry Formulations", Second Edition, 1989, pp. 737-744. Such coarse hand cleaners are used without addition of water, cleansing exclusively being effected by means of the product and a drying cloth.

To remove soiling of skin and hands caused by printing colors and/or inks, especially printer inks, skin and hand cleansing preparations are available on the market, which include sodium dithionite and cocamide DEA (cocamide diethanolamine). In particular, the product available from Stockhausen under the trade name of STOKOMIN II was found to be highly effective on soiling of skin and hands caused by inks.

However, the degree of soil removal has been found to be in direct relation with the content of free diethanolamine which, associated with the production, comes from the type of cocamide DEA used in each case. Thus, for example, the use of cocamide DEA types (Comperlan COD) having a free diethanolamine content of <2 wt.-% in the final product gives significantly poorer cleaning results. It has also been found that, when using cocamide DEA types, a content of free diethanolamine of >1.2 wt.-% in the final product is necessary to bring about effective removal of soiling on skin and hands caused by printing colors and/or inks, especially printer inks.

From scientific studies, however, diethanolamine is known to involve some risk of sensitization, which is why national legislators have established limiting values restricting the use of diethanolamine in cosmetic products. Thus, for example, the German decree on cosmetics has settled that the content of free diethanolamine in cosmetics must not exceed a maximum of 0.5 wt.-%, relative to the final product.

In view of the diverse qualities of printing colors and/or inks, especially of printer inks, available on the market and the tenacious soiling of skin and hands caused by same, which often resists cleaning by means of conventional skin cleansing agents, there is still a demand for skin or hand cleansing agents, which would be largely free of free diethanolamine in the cleansing product and show a cleaning effect comparable to or better than that of products well-known in the prior art with a content of free diethanolamine of >1.2 wt.-%, for effective removal of soiling on skin and hands caused by printing colors and/or inks, especially printer inks.

The object was therefore to provide skin and hand cleansing agents, particularly for cleaning extreme soiling of skin and hands caused e.g. by reducible or oxidizable printing colors and/or inks, which agents would have a cleaning effect comparable to that of products available in the prior art, but should have a content of free diethanolamine of <0.5 wt.-%. Moreover, said skin and hand cleansing agent should be stabilized in such a way that a homogeneous and stable final product would be formed.

Surprisingly, said object was accomplished by means of a skin and hand cleansing agent, particularly for the removal of printing colors and/or inks, especially printer inks, comprising the components
a) 1 to 70 wt.-% of at least one ethoxylated amine and/or ethoxylated diamine,
b) 30 to 70 wt.-% of at least one polyethylene glycol of general formula $H-O-(CH_2CH_2-O)_n H$, wherein n is an integer of from 1 to 150,
c) 1 to 30 wt.-% of at least one fatty alcohol polyglycol ether,
d) 0.1 to 5 wt.-% of at least one complexing agent,
e) 0 to 30 wt.-% of at least one reducing or oxidizing agent,
f) 0 to 25 wt.-% of one or more abrasives,
g) 0 to 10 wt.-% of at least one polyhydric alcohol,
h) 0 to 3 wt.-% water,
i) optionally one or more viscosity-building agents,
j) optionally further cosmetic adjuvants, additives and/or active substances,
the sum of components a) through j) making 100 wt.-%, relative to the composition of the cleansing agent.

More specifically, ethoxylated amines according to the general formula

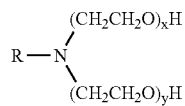

can be used as component a), wherein
R represents a saturated, unsaturated, branched or unbranched alkyl residue having 1 to 24 C atoms, and
x and y are integers of from 1 to 30, and can be x=y or x≠y, and the sum x+y≦60.

The ethoxylated amine is preferably selected from the group of oleylamines, tallow amines and cocamines, with those oleylamines, tallow amines and cocamines having the indices x+y=2.5 or 15, i.e., 2.5 or 15 EO units, being particularly preferred. Such ethoxylated tertiary aliphatic amines are available from the company AKZO NOBEL under the trade name of Ethomeen®. The following commercial products should be mentioned by way of example:

| | |
|---|---|
| Ethomeen ® C/12 | (INCI: PEG-2 cocamine) |
| Ethomeen ® C/15 | (INCI: PEG-5 cocamine) |
| Ethomeen ® C/25 | (INCI: PEG-15 cocamine) |
| Ethomeen ® 18/12 | (INCI: PEG-2 stearamine) |
| Ethomeen ® 18/15 | (INCI: PEG-5 stearamine) |
| Ethomeen ® 18/25 | (INCI: PEG-15 stearamine) |
| Ethomeen ® OV/1 | (INCI: PEG-2 oleamine) |
| Ethomeen ® S/12 | (INCI: PEG-2 soyamine) |
| Ethomeen ® S/15 | (INCI: PEG-5 soyamine) |
| Ethomeen ® S/25 | (INCI: PEG-15 soyamine) |
| Ethomeen ® T/12 | (INCL: PEG-2 tallow amine) |
| Ethomeen ® T/25 | (INCI: PEG-15 tallow amine) |

In a preferred fashion, Ethomeen® C/12, Ethomeen® S/12 and Ethomeen® T/12 are employed as ethoxylated tertiary amine, with the commercial product Ethomeen® OV/12 being particularly preferred according to the invention.

The ethoxylated diamines of component a) are preferably diamines according to the general formula II

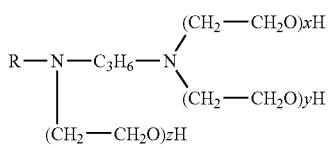

wherein
R=saturated, unsaturated, branched or unbranched alkyl residue having 1 to 24 C atoms, and
x, y and z are integers of from 1 to 10, and x=y=z, or x, y and z are different from each other, and the sum x+y+z≦30.

The commercial products available under the trade name of Ethoduomeen® from the company Akzo Nobel may be mentioned by way of example.

According to the invention, 30 to 70 wt.-%, preferably 40 to 65 wt.-%, and more preferably 50 to 60 wt.-%, relative to the composition of said skin and hand cleansing agent, of at least one polyethylene glycol of general formula H—O—(CH$_2$CH$_2$—O)$_n$H wherein n is an integer of from 1 to 150, preferably an integer of from 1 to 25, can be used as component b).

Polyethylene glycols with a molecular weight of from 200 to 1000 can be used with advantage. In this context, polyethylene glycols with a molecular weight of 400 were found to be particularly advantageous. For example, such polyethylene glycols which, inter alia, find extensive use as technical solvents, are available from BASF AG, Ludwigshafen, Germany, under the trade name of Lutrol®.

Furthermore, the skin and hand cleansing agent according to the invention includes 1 to 30 wt.-%, preferably 1 to 20 wt.-%, and more preferably 3 to 15 wt.-%, relative to the composition of said skin and hand cleansing agent, of at least one fatty alcohol polyglycol ether as component c). Such fatty alcohol polyglycol ethers which, inter alia, find use as emulsifiers, wetting agents and dispersing agents in the chemical-technical industry, are non-ionic surfactants which can be obtained in a well-known manner by reacting ethylene oxide and e.g. fatty alcohols. Both technically produced and native fatty alcohols are used as starting materials in the production of said fatty alcohol polyglycol ethers. For example, coconut fatty alcohol and oleyl alcohol or native fatty alcohols with an iodine number of 50, having 12 to 18, or predominantly 18, carbon atoms in the alcohol molecule, may be mentioned as suitable fatty alcohols.

The fatty alcohol ethoxylates used as component c) preferably have the general formula

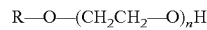

R—O—(CH$_2$CH$_2$—O)$_n$H wherein
R is a saturated, unsaturated, branched or unbranched alkyl residue, and n is an integer of from 1 to 11.

In a preferred fashion, an alkyl residue having 8 to 18 carbon atoms, especially C$_{10}$ to C$_{16}$, and especially preferably C$_{11}$ to C$_{14}$, is used as saturated, unsaturated, branched or unbranched alkyl residue, with n preferably being an integer of from 3 to 10, and particularly an integer of from 5 to 7.

The skin and hand cleansing agents according to the invention may preferably include laureth-6 as fatty alcohol ethoxylate.

In one embodiment particularly preferred according to the invention, the skin and hand cleansing agents may include the fatty alcohol polyglycol ethers marketed by the company Sasol Servo Delden under the brand of INTRASOL®, preferably the non-ionic surfactants designated INTRASOL® FA 12/18/5, which are based on a fatty alcohol with 12 to 18 carbon atoms and have 5 EO units.

As component d), the skin and hand cleansing agents according to the invention imperatively include 0.1 to 5 wt.-%, preferably 0.5 to 4 wt.-%, relative to the composition of said skin and hand cleansing agent, of at least one complexing agent.

Complexing agents or chelating agents are conventionally used in the field of cosmetics and in medical pharmaceutical technology and serve to prevent undesirable chemical reactions in cosmetic or pharmaceutical formulations by complexing interfering metal ions.

Among other things, the complexing or chelating agents in the skin and hand cleansing agents according to the invention assume the function of converting the printing colors and/or ink dyes responsible for soiling of skin and hands into soluble complexes, thereby allowing effective removal thereof from the skin. According to the invention, all complexing agents usable in complexing or masking of printing color and/or ink dyes can therefore be used. For example, well-known complexing agents are polycarboxylic acids, polyamines, crown ethers, cryptands, etc. More specifically, tartaric and citric acid and salts thereof, aminopolycarboxylic acids and salts thereof, such as ethylenediaminetetraacetic acid (EDTA), nitrilotriacetic acid (NTA), hydroxyethylenediaminetriacetic acid (HOEDTA) and salts thereof, diethyleneaminepentaacetic acid (DPTA) and salts thereof, methylglycinediacetic acid (MGDA) and salts thereof, iminodisuccinic acid and salts thereof, trans-1,2-diaminocyclohexanetetraacetic acid (CDTA) and salts thereof, polyaspartic acid and salts thereof, but also so-called builders and cobuilders such as polycarboxylates or polyphosphates can be used. In a preferred fashion, the skin and hand cleansing agents of the invention include EDTA, the tetrasodium salt of iminodisuccinic acid (tetrasodium iminodisuccinate) and sodium polyaspartate as complexing agents, with a content of complexing agents or mixture of complexing agents of 2 wt.-%, relative to the skin and hand cleansing agent, being particularly preferred.

In addition to components a) through d) imperatively included in the skin and hand cleansing agents according to the invention, the skin and hand cleansing agents optionally may include further components e) through j) allowing advantageous improvement of the cleaning result.

Thus, depending on the type of soiling on skin and hands, the skin and hand cleansing agents according to the invention may have 0 to 30, preferably 1 to 25 wt.-%, and more preferably 3 to 20 wt.-%, of at least one reducing or oxidizing agent as component e). For effective removal of a variety of reducible printing colors and/or inks, especially printer inks, dithionites or hydrosulfites such as sodium dithionite can be used, which have been known for such purposes for years. In a particularly preferred embodiment of the invention the skin and hand cleansing agents according to the invention include 8 to 12 wt.-% sodium dithionite as reducing agent.

Compounds liberating peroxide can be used as oxidizing agents. For example, such oxidizing agents are mentioned in U.S. 2002/0013237 A1 which hereby is fully incorporated in the description of the present patent application. The above U.S. 2002/0013237 A1 relates to skin cleansing agents for the removal of inks and other stains from arms and hands, which agents include effective amounts of a low-molecular weight monohydric alcohol with 1 to 12 carbon atoms and a peroxide-liberating agent such as a perborate salt, preferably sodium perborate, so as to effect removal of the ink from the skin by a synergistic reaction of the alcohol with the perborate salt. More specifically, it is only upon contact of the cleansing agent with said ink soiling that this synergistic reaction should be triggered, which then is responsible for the removal of the ink soiling. The skin and hand cleansing agents described therein include 40 to 80 wt.-%, relative to the overall amount of skin and hand cleansing agent, of preferably ethanol or isopropanol, particularly because polyhydric alcohols, but also ether- and ester-substituted alcohols fail to trigger a synergistic reaction to such an extent that effective removal of the ink soilings would be ensured.

It should be noted in this context that the skin and hand cleansing agents of the invention which comprise the components a) through d) achieve effective removal of soiling on skin and hands caused by printing colors and inks, the cleaning effect or the removal of dye apparently being largely due to the presence of component a), i.e., the proportion of ethoxylated amine and/or ethoxylated diamine, or, a synergistic interaction of components a) through d) is to be assumed. Moreover, the skin and hand cleansing agents of the invention do not include any monohydric alcohols such as ethanol or isopropanol with a content of ≧40 wt.-%, relative to the overall amount of cleansing agent, so that synergistic reaction in accordance with U.S. 2002/0013237 A1 cannot take place if a skin and hand cleansing agent according to the invention includes a perborate salt such as sodium perborate as oxidizing agent as a supporting cleaning component.

Although the skin and hand cleansing agents according to the invention have high cleansing efficiency, so that addition of abrasives to these cleansing agents is dispensable, the skin and hand cleansing agents may optionally include abrasives as component f) in particular cleansing applications. In this event, the percentage of abrasive or abrasives can be 0 to 25 wt.-%, relative to the composition of the cleansing agent, and preferably 10 to 20 wt.-%.

For example, abrasives to be used with preference are plastic abrasive agents based on polyethylene or polyurethane, vegetable meals such as corn-cob meal, wheat bran, oatmeal and wood meal, abrasive agents based on natural stone and/or shell meals, particularly meals of walnut shells, almond shells, hazelnut shells, meals of olive, apricot or cherry stones, or any mixture of these shell and stone meals and beads of waxes, e.g. jojoba waxes, with bleached meals, especially hydrogen peroxide-bleached walnut shell meal being particularly preferred, which can be used with advantage in the removal of pigment soiling of the respective printing colors or printer inks.

As component g), the skin and hand cleansing agents according to the invention include at least 0 to 10 wt.-%, preferably 1 to 5 wt.-% of a polyhydric alcohol. For example, such polyhydric alcohols are straight-chain, branched or cyclic alkanols with 2 to 12, preferably 2 to 6 carbon atoms, with glycerol and/or 1,2-propanediol being particularly preferred.

In another embodiment of the invention, the skin and hand cleansing agents according to the invention may optionally include 0 to 3 wt.-% water as component h) and 0 to 10 wt.-% of one or more viscosity-building agents as component i). For example, such viscosity-building agents or thickening agents are organophilic and/or hydrophilic layer silicates, particularly bentonites, polysaccharides such as cellulose, guar meal and/or xanthans, modified polysaccharides, preferably cellulose ethers, carboxymethylcellulose and/or hydroxyalkylcelluloses, preferably hydroxyethylcellulose, alginates and/or inorganic electrolytes, preferably sodium chloride and/or magnesium sulfate, and/or pyrogenic silica available from Degussa AG under the trade name of Aerosil®, for example. Preferably, the skin and hand cleansing agents may include 0 to 5 wt.-%, preferably 0 to 3 wt.-% of modified hydrophobic celluloses, such as cetyl myristyl hydroxyethyl ethylcellulose, which can be obtained from AKZO NOBEL under the trade name of Elfacos® CDHM. Particularly preferred is a combination of pyrogenic silica such as Aerosil® 200 and modified hydrophobic Elfacos® type celluloses.

As components j), the skin and hand cleansing agents according to the invention may optionally include further cosmetic adjuvants, additives and/or active substances, e.g. pH regulators, stabilizers, preferably cetearyl alcohol and/or hydrogenated castor oils, such as trihydroxystearin, odorous substances, preservatives, preferably organic acids, and antioxidants such as vitamin E acetate, and/or oily or aqueous care components.

The inventive skin and hand cleansing agents, especially coarse hand cleaners, are produced in a batch or continuous process using well-known devices, the skin and hand cleansing agents preferably being obtained in the form of creamy agents or flowable viscous pastes. Suitable devices are heatable vessels equipped with stirrer, mixer, as well as extruders.

Skin and hand cleansing agents preferred according to the invention have the following composition:

| Component | | Wt.-% |
|---|---|---|
| a) | Ethoduomeen OV 13 and/or Ethomeen OV 12 | 10.0 to 20.0 |
| b) | Polydiol 400 | 40.0 to 60.0 |
| c) | Intrasol FA 1218/10 | 5.0 to 10.0 |
| d) | EDTA | 1.0 to 2.0 |
| e) | Na dithionite | 5.0 to 15.0 |
| f) | walnut shell meal, bleached | 5.0 to 10 |
| g) | 1,2-Propanediol and/or glycerol | 1.0 to 3 |
| i) | Elfacos ® CDHM | 0.5 to 1.0 |
|  | Aerosil ® 200 | 1.0 to 3.0 |
| j) | Perfume oil | 0.5 |

Surprisingly, it was possible to demonstrate that when using such skin and hand cleansing agents having a content of free diethanolamine of <0.5 wt.-%, said agents would achieve a cleaning effect comparable to that of e.g. commercially available products having a content of free diethanolamine of up to 2.8 wt.-%.

The invention claimed is:

1. A skin cleansing agent comprising:
   a) 10 to 70 wt.-% of at least one ethoxylated amine and/or ethoxylated diamine,
   b) 30 to 70 wt.-% of at least one polyethylene glycol of general formula H—O—(CH$_2$CH$_2$—O)$_n$H, wherein n is an integer of from 1 to 150,
   c) 1 to 30 wt.-% of at least one fatty alcohol polyglycol ether,
   d) 0.1 to 5 wt.-% of at least one complexing agent,
   e) 0 to 30 wt.-% of at least one reducing or oxidizing agent,
   f) 0 to 25 wt.-% of one or more abrasives,
   g) 0 to 10 wt.-% of at least one polyhydric alcohol,
   h) 0 to 3 wt.-% water,
   i) optionally one or more viscosity-building agents,
   j) optionally one or more further cosmetic adjuvants, additives and/or active substances,
   the sum of components a) through j) making 100 wt.-% of the cleansing agent.

2. The skin cleansing agent according to claim 1, comprising an ethoxylated amine wherein the ethoxylated amine is an amine in accordance with general formula I

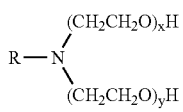

wherein
R = saturated, unsaturated, branched or unbranched alkyl residue having 1 to 24 C atoms, and
x and y are integers of from 1 to 30, and can be x = y or x ≠ y, and the sum x+y ≦ 60.

3. The skin cleansing agent according to claim 1, comprising an ethoxylated amine wherein the ethoxylated amine is selected from the group of oleylamines, tallow amines, and cocamines.

4. The skin cleansing agent according to claim 1, comprising an ethoxylated diamine wherein the ethoxylated diamine is a diamine according to the general formula II

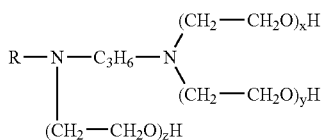

wherein
R = saturated, unsaturated, branched or unbranched alkyl residue having 1 to 24 C atoms, and
x, y, and z are integers of from 1 to 10, and x=y=z, or x, y, and z are different from each other, and the sum x+y+z ≦ 30.

5. The skin cleansing agent according to claim 1, wherein as component b), the agent includes 40 to 65 wt.-% of at least one polyethylene glycol of general formula H—O—(CH$_2$CH$_2$—)$_n$H, wherein n is an integer of from 1 to 150.

6. The skin cleansing agent according to claim 5, wherein as component b), the agent includes 50 to 60 wt.-% of at least one polyethylene glycol of general formula H—O—(CH$_2$CH$_2$—)$_n$H, wherein n is an integer of from 1 to 25.

7. The skin cleansing agent according to claim 1, wherein the agent includes 1 to 20 wt.-% of at least one fatty alcohol polyglycol ether as component c).

8. The skin cleansing agent according to claim 7, wherein component c) is at least one fatty alcohol ethoxylate of general formula R—O—(CH$_2$CH$_2$—O)$_n$H
wherein
R is a saturated, unsaturated, branched or unbranched alkyl residue, and n is an integer of from 1 to 11.

9. The skin cleansing agent according to claim 1, wherein the agent includes 0.1 to 4 wt.-% of at least one complexing agent as component d).

10. The skin cleansing agent according to claim 1, wherein the agent includes 2 wt.-% of at least one complexing agent as component d).

11. The skin cleansing agent according to claim 1, wherein the agent includes 1 to 25 wt.-% of at least one reducing or oxidizing agent as component e).

12. The skin cleansing agent according to claim 11, wherein the agent has dithionites as reducing agents.

13. The skin cleansing agent according to claim 12, wherein the agent includes 8 to 12 wt.-% sodium dithionite as reducing agent.

14. The skin cleansing agent according to claim 11, wherein the agent includes at least one perborate salt as oxidizing agent.

15. The skin cleansing agent according to claim 1, wherein the agent includes 10 to 20 wt.-% abrasives as component f).

16. The skin cleansing agent according to claim 1, wherein the agent includes 1 to 5 wt.-% of at least one polyhydric alcohol as component g), which is a straight-chain, branched or cyclic alkanol having 2 to 12 carbon atoms.

17. The skin cleansing agent according to claim 1, wherein as component i), the agent includes a combination of cetyl myristyl hydroxyalkylcellulose and pyrogenic silica as viscosity-building agent.

18. The skin cleansing agent according to claim 1 wherein as component j), the agent includes pH regulators, stabilizers, odorous substances, preservatives, antioxidants and/or oily or aqueous care components as cosmetic adjuvants, additives and/or active substances.

19. The skin cleansing agent according to claim 1, which does not include 40 wt.-% or more of one or more monohydric alcohols relative to the total weight of the cleansing agent.

20. A method for the removal of printing colors and/or inks from the skin, comprising contacting printing colors and/or inks on the skin with the skin cleansing agent according to claim 1.

21. The skin cleansing agent according to claim 1, wherein component b) includes at least one polyethylene glycol of general formula H—O—(CH$_2$CH$_2$—O)$_n$H, wherein n is an integer of from 8 to 150.

22. The skin cleansing agent according to claim 1, which contains no monohydric alcohols having 1 to 12 carbon atoms.

* * * * *